United States Patent [19]

Christensen

[11] Patent Number: Plant 5,703

[45] Date of Patent: Apr. 1, 1986

[54] HYBRID MINIATURE ROSE PLANT CV. AROYUMI

[75] Inventor: Jack E. Christensen, Ontario, Calif.

[73] Assignee: Armstrong Nurseries, Inc., Ontario, Calif.

[21] Appl. No.: 640,255

[22] Filed: Aug. 13, 1984

[51] Int. Cl.[4] ..... A01H 5/00

[52] U.S. Cl. ..... Plt./7

[58] Field of Search ..... Plt./7

*Primary Examiner*—Robert E. Bagwill

*Attorney, Agent, or Firm*—Synnestvedt & Lechner

[57] ABSTRACT

A new, hardy hybrid miniature rose especially suited for garden decoration. The new cultivar bears large, multicolored flowers held well above the foliage in regular, rounded clusters. Flower petals are dropped cleanly before they can age to an unattractive off-color. The new variety is easy to grow, producing an abundance of large, vigorously growing deep-green foliage which covers the plant attractively.

1 Drawing Figure

This invention relates to a new variety of hybrid miniature rose plant cv. Aroyumi. The plant is a hardy outdoor seedling of the miniature bush type, cultivated for garden decoration. It was first discovered and asexually reproduced by Jack E. Christensen in Ontario, Calif., having as its seed parent Golden Angel (U.S. Plant Pat. No. 4,028) and as its pollen parent Cricket (U.S. Plant Pat. No. 4,663).

The new rose cv. Aroyumi is particularly distinguishable from other presently commercialized rose cultivars by the following combination of characteristics: is rounded, compact habit; is abundant production of large, multicolored flowers held well above the foliage; its abundant, large deep-green foliage that attractively covers the plant; its ability to drop old petals cleanly before they can age to an unattractive off-color; and its vigorous growth, which makes the plant easy to grow. Aroyumi holds these distinguishing characteristics through succeeding propagations by cuttings and budding.

This new rose cultivar may be distinguished from its seed parent, Golden Angel (U.S. Plant Pat. No. 4,028), by the following combination of characteristics: Golden Angel produces flowers of a relatively uniform yellow color, whereas the new rose produces flowers that begin as yellow but blush to pinkish red, essentially as described and illustrated herein. Aroyumi bears flowers with 18 to 25 petals, whereas the seed parent produces flowers with significantly heavier petalage (60 to 70 petals). Whereas the new rose bears flowers of 1½ to 2 inches in diameter, Golden Angel bears significantly smaller flowers of 1 to 1½ inches in diameter.

Aroyumi may be distinguished from its pollen parent, Cricket (U.S. Plant Pat. No. 4,663), by the following combination of characteristics: Cricket produces flowers of a relatively uniform, bright orange coloration, whereas the new cultivar produces flowers of a yellow coloration blushing to pinkish red, essentially as described and illustrated herein. Aroyumi bears flowers of 1½ to 2 inches in diameter, whereas the pollen parent bears significantly smaller flowers of 1 to 1½ inches in diameter. Whereas the new rose produces a mature bush of a medium-low, compact habit with medium-caliper canes, Cricket produces a mature bush of a medium-tall, less compact habit with larger caliper canes.

The accompanying drawing illustrates the new variety in color as grown in Ontario, Calif., and shows the flowering thereof from bud to full bloom.

Throughout this specification, color names beginning with a small letter signify that the name of that color as used in common speech is aptly descriptive. Color names beginning with a capital letter designate values based on the R.H.S. Colour Chart published by The Royal Horticultural Society of London, England.

The descriptive matter which follows pertains to roses grown in Ontario, Calif. and is believed to apply to similar conditions of soil and climate elsewhere.

FLOWER

The new variety bears its flowers sometimes singly, usually 2 to 3 flowers or more per stem, in regular, rounded clusters on stems of normal strength and of short to medium length for the class. Outdoors, the plant blooms very abundantly and nearly continuously throughout the growing season. The flowers have a slight fruity fragrance.

BUD

The peduncle is short to average in length for the class, of average to heavy caliper, strong, erect, and stiff. It is moderately rough with numerous stipitate glands and is between Yellow-Green 147A and Green 137C in color.

Before the calyx breaks, the bud is medium to large in size for the class, of medium length, and pointed to ovoid to globular in form. There are few foliaceous appendages and stipitate glands on the surface of the bud. There are usually slender foliaceous parts present which extend beyond the tip of the bud, equal to one quarter or more of its length.

As the calyx breaks, bud color is between Yellow-Orange 15B and Yellow 13B; areas exposed to sunlight blush to as deeply as between Red 42A and Red 45C. The inner surface of the sepals is lined with a fine woolly tomentum; sepal margins are lined with stipitate glands.

As the first petal opens, the bud is average to large in size for the class, of medium length, and pointed to ovoid to globular in form. The color of the outside petal surface is between Yellow-Orange 15B and Yellow 13B; areas exposed to sunlight blush to as deeply as between Red 42A and Red 45C. The color of the inside petal surface is the same as the outside surface with little blushing. The bud opens up well and is not prevented from opening by cold, hot, wet, or dry weather.

BLOOM

The size of the bloom when fully open is average to large for the class, ranging from 1½ to 2 inches in diameter. Petalage is double with the petals arranged regularly; petals number from 18 to 25, and there may be from 1 to 3 petaloids present. Bloom form when half open is moderately high-centered to cupped to globular, with petals moderately cupped and with petal edges moderately reflexed to rolled outward. When fully open, the bloom is cupped, with petals more loosely cupped and petal edges very rolled to quilled outward.

Petals are of moderately heavy substance and of medium thickness, slightly satiny inside and slightly shiny outside. The outside petals are broadly obovate with rounded apices. Intermediate petals are nearly obovate with rounded apices. Inside petals are narrowly obovate to irregular with rounded apices. Colors of all petals may be modified by being bordered or margined or blotched or shaded or washed or tinted with other colors.

The following paragraph describes the color values observed in a newly opened flower from a plant of the new variety grown outdoors in Ontario, Calif., during the month of November.

The outside surface of the outside petals is between Yellow-Orange 15C and Yellow 13B in color; areas exposed to sunlight blush to as deeply as between Red 42C and Red 45D. The inside surface of the outside petals is between Yellow-Orange 15C and Yellow 13B in color; areas exposed to sunlight blush to as deeply as between Orange-Red 32C and Red 41C. The outside surface of the intermediate petals has the same color as the outside surface of the outside petals with less blushing. The inside surface of the intermediate petals has the same color as the inside surface of the outside petals with less blushing. The outside surface of the inner petals has the same color as the outside surface of the outside petals with little or no blushing. The inside surface of the inner petals has the same color as the inside surface of the outside petals with little or no blushing.

The following paragraph describes the color values observed in a flower from a plant grown outdoors in Ontario, Calif., that had been open for three days in the month of November.

The outside surface of the outside and inside petals is between Yellow 12B and Yellow 9C in color. The inside surface of the outside and inside petals has the same color as the outside surface of the outside and inside petals, the majority of the petal surface having blushed to between Red 47C and Red 47A.

The general color effect of the newly opened flower is predominantly between Yellow-Orange 15C and Yellow 13B, with the outer petals blushing to between Orange-Red 32C and Red 41C. Three days after opening, the general color effect of the flower is predominantly between Red 47A and Red 47C, with some yellow tones toward the flower center between Yellow 12B and Yellow 9C.

Petals usually drop off cleanly and are not particularly affected in this respect by cold, hot, wet, or dry weather. Flowers last on the bush in the garden from 4 to 5 days during the month of November in Ontario, Calif. Flowers cut from plants grown outdoors in the month of November last from 4 to 5 days at living-room temperatures.

REPRODUCTIVE ORGANS

Stamens are average to many in number and are arranged regularly about the pistils. Filaments are of medium length, and many to most have anthers. The anthers are of medium size, and all open approximately at once. Anther color when immature is near Yellow-Orange 17C; the color of the mature anthers is near Greyed-Orange 166A. Pollen is moderate to abundant in quantity and near Yellow-Orange 14C in color.

Pistils are average in number (approximately 35). Styles are uneven, short to average in length, of average to heavy caliper, and somewhat bunched. Stigma color is near Yellow 2B. The ovaries are usually all enclosed in the calyx.

Hips are average in length and ovoid to globular in form. Hip color is near Orange-Red 32A. The hips are moderately smooth with thick, fleshy walls.

Sepals fall soon.

Seeds are average to many in number (8 to 15) for the class and are of medium size.

FOLIAGE

The compound leaves are usually comprised of 3 to 5 leaflets. They are borne in very abundant quantities and are medium to large in size for the class. Leaves are moderately heavy and semi-glossy. Leaflets are nearly oval in shape with acute apices and round bases. Leaflet margins are irregularly serrate.

The color of the upper surface of the mature foliage is between Yellow-Green 147A and Green 136A; the under surface of the mature foliage is of a color between Yellow Green 147B and Green 138B. The upper surface of the young foliage is between Yellow-Green 146A and Green 136B in color, lightly washed with near Greyed-Purple 183A; the under surface of the young foliage displays a coloration between Yellow-Green 146C and Green 138B, lightly washed with near Greyed-Purple 183A.

The rachis is average in size. Its upper side is grooved with some stipitate glands on the edges, while the under side is moderately prickly, with stipitate glands.

Stipules are of medium length, moderately narrow with points that are medium to long in length, turning out at an angle of more than 45°.

The plant displays an above-average resistance to mildew and rust as compared with other cultivars now in commerce grown under comparable conditions at Ontario, Calif.

GROWTH

Plants of the new variety are miniatures, bushy and much-branched, yet compact and upright in habit. The canes are of medium caliper for the class. Plant growth is very vigorous.

The main stems are between Yellow-Green 146A and Green 138A in color and bear very few large prickles. The large prickles are of medium length for the class and are almost straight, with narrow bases of medium length. Their color is near Greyed-Orange 165B. There are no small prickles and no hairs.

Branches are between Yellow-Green 144A and Green 137A in color; they bear very few large prickles of medium length for the class. These are almost straight, with narrow bases of medium length, and of a color near Greyed-Orange 164C. There are no small prickles and no hairs.

New shoots are of the same color as the branches, washed lightly with near Greyed-Purple 183A. They bear very few large prickles of medium length for the class which are almost straight and have narrow bases of medium length. Prickle color is near Greyed-Purple 183A. There are no small prickles and no hairs.

I claim:

1. A new and distinct variety of rose plant of the hybrid miniature class, essentially as herein illustrated and described, being particularly characterized by its rounded, compact habit; its abundant production of large, multicolored flowers held well above the foliage; its abundant, large deep-green foliage that attractively covers the plant; its ability to drop old petals cleanly before they can age to an unattractive off-color; and its vigorous growth.

* * * * *

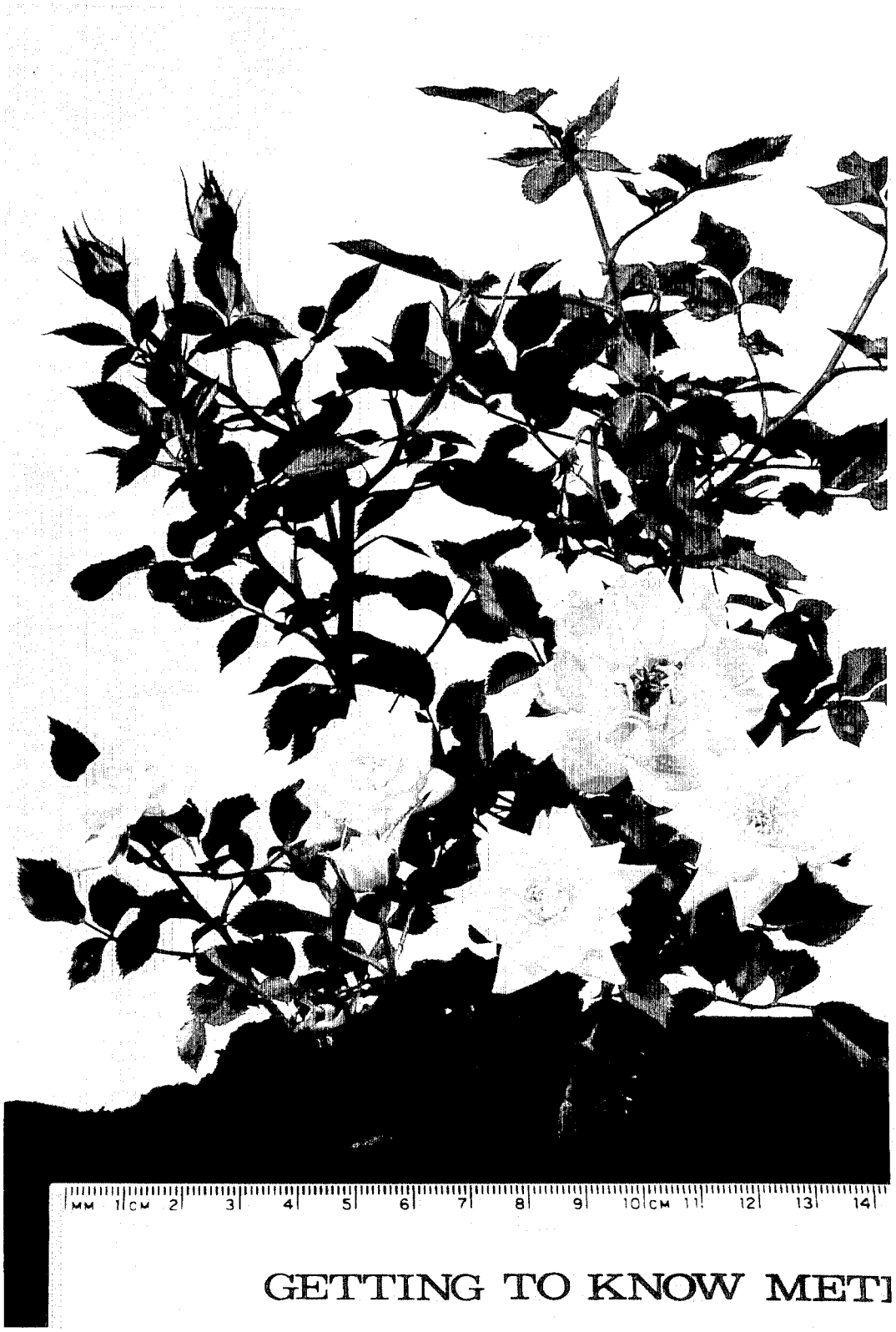
MM 1 CM 2 3 4 5 6 7 8 9 10 CM 11 12 13 14
GETTING TO KNOW METI